United States Patent [19]
Sebring

[11] Patent Number: 5,156,166
[45] Date of Patent: * Oct. 20, 1992

[54] MEDICAL PATIENT SUPPORT TABLE
[75] Inventor: John P. Sebring, Townsend, Mass.
[73] Assignee: John K. Grady, Harvard, Mass.
[*] Notice: The portion of the term of this patent subsequent to Oct. 2, 2007 has been disclaimed.
[21] Appl. No.: 497,234
[22] Filed: Mar. 22, 1990

Related U.S. Application Data
[62] Division of Ser. No. 229,488, Aug. 8, 1988, Pat. No. 4,960,271.

[51] Int. Cl.$^5$ ............................................. A61G 13/00
[52] U.S. Cl. ..................................... 128/845; 378/209
[58] Field of Search ............................. 269/323–328; 5/60–62; 128/653, 845; 378/209

[56] References Cited
U.S. PATENT DOCUMENTS

| | | | |
|---|---|---|---|
| 3,302,022 | 1/1967 | Brenner et al. | 269/60 |
| 3,396,274 | 8/1968 | Hogan | 269/323 |
| 4,153,841 | 5/1979 | Kok | 378/178 |
| 4,452,439 | 6/1984 | Hogan | 269/323 |
| 4,475,072 | 10/1984 | Schwehr | 269/323 X |
| 4,578,833 | 4/1986 | Vrzalik | 5/61 |
| 4,866,796 | 9/1989 | Robinson et al. | 269/323 X |
| 4,912,754 | 3/1990 | van Steenburg | 378/209 |
| 4,958,817 | 9/1990 | Heller et al. | 269/323 X |
| 4,960,271 | 10/1990 | Sebring | 269/323 |

Primary Examiner—Robert A. Hafer
Assistant Examiner—Kerry Owens
Attorney, Agent, or Firm—James H. Grover

[57] ABSTRACT

A cantilever mounted table for an X-ray patient undergoing procedures requiring tilting the table head to foot or canting the table about its longitudinal axis allows a medical team free axis to one side and an end of the patient, and provides an improved collision sensing switch in the event the table stikes an obstruction below.

4 Claims, 3 Drawing Sheets

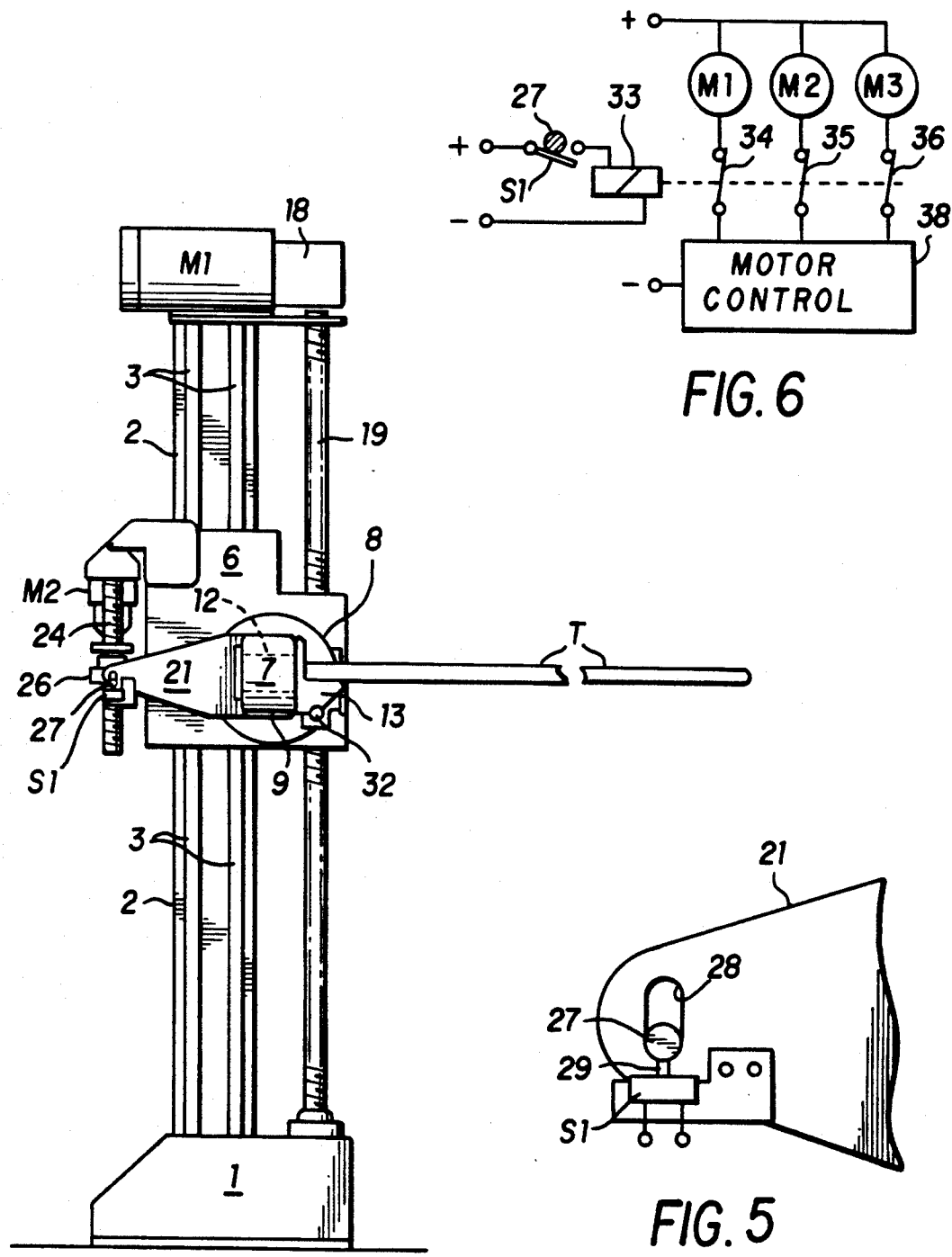

MEDICAL PATIENT SUPPORT TABLE

This application is a division of pending application Ser. No. 07/229,488, filed Aug. 8, 1988, now U.S. Pat. No. 4,960,271.

BACKGROUND OF THE INVENTION

This invention involves apparatus for supporting a patient on a table during medical procedures under X-ray observation such as surgery, catheterization and dye angiography, or treatment of a patient in trauma. These procedures usually involve an anesthesiologist and a team of physicians and nurses around a table supporting the patient, and require space for an X-ray tube and receptor to be moved into and out of unlimited positions around the patient, while allowing the medical team free access to at least one side of the table, and allowing the anesthesiologist ready access to the head of the patient. The support apparatus should further be capable of tilting the patient around a transverse axis to raise or lower his head, and canting the patient by rotation generally around his longitudinal axis. However such movements may risk collision of the underside of the patient table with the floor, or equipment on the floor under the table. Collision sensing switches under the table have proven unsatisfactory because they may be inadvertently disabled by straps used to secure the patient to the table.

It has been proposed to support a patient table by a connection offset from the longitudinal axis of the table, but this proposal, although generally satisfactory, causes movement of the patient's head relative to the anesthesiologist during tilting and canting, and increases the possibility of collision below the table.

Accordingly it is an object of the invention to provide patient support apparatus which allows both tilting and canting of the patient by a simplified and more economical and efficient mechanism, and with decreased risk of collision below the patient table.

A further object is to provide patient support apparatus which, without alteration of its components, can be adapted to extend either to the right or left side of its base and standard.

SUMMARY OF THE INVENTION

According to the invention apparatus for supporting a patient during medical procedures comprises a base with an upright standard, a cantilever beam extending horizontally from the standard and having a longitudinal axis, an elongate patient table extending at a right angle to the beam, a rotative attachment of the table to the free end of the beam to cant the table around an axis parallel to the length of the table, and a rotative coupling of the beam to the standard to tilt the table around an axis transverse of the table so that a patient on the table can be both canted about a head to foot axis, and tilted head up or head down about a transverse axis.

Further according to the invention the apparatus includes a motor for turning the beam about its longitudinal axis and tilting the table, an additional motor for canting the table about its longitudinal axis, a crank extending laterally from the beam, a drive link between the motor and the crank, a loose coupling of the link to the crank, and a switch sensing movement of the crank relative to the link to disconnect power to either of the motors when the table collides with an obstruction below.

Still further according to the invention the end of the beam comprises a constant diameter collar extending at right angles to the beam between identical open ends, and a plate rotatively supported in the collar and having means for attachment to the table, the plate being adapted to fit in either open end of the collar so that the table can be rotatively attached at either side of the beam and extend to the right or left of the standard.

DRAWINGS

FIG. 4 is an end elevation of the apparatus;

FIG. 5 is an enlarged view of a detail of FIG. 4 showing an electrical collision switch;

FIG. 6 is an electrical diagram of a circuit connected to the collision switch;

DESCRIPTION

Figure 1:
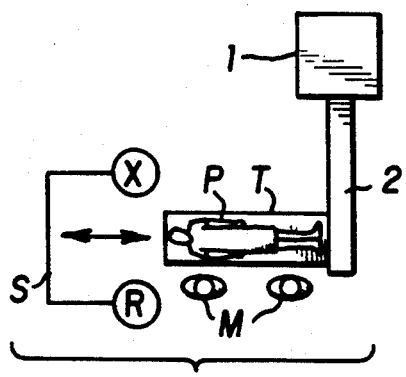
FIGS. 1 and 2 are diagrammatic views of two positions of a patient table relative to a cantilever beam of support apparatus according to the invention.
Figure 2:
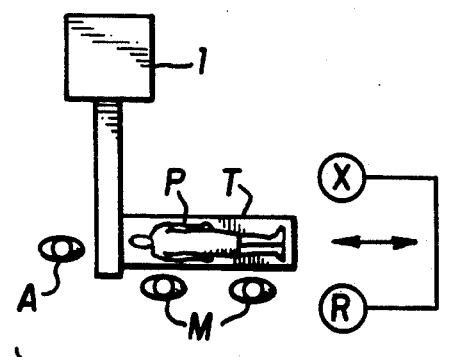

FIGS. 1 and 2 show diagrammatically two alternative overhead dispositions of patient support during X-ray observation. In FIG. 1 the patient P is positioned on a cantilever table T with his feet adjacent the left side of a beam 2 extending from a standard 1. A stand S for an X-ray source X and an X-ray receptor R is moveable from the head toward the feet of the patient. Medical personnel M have the most advantageous access to the head and thorax of the patients being catheterized in cardiac procedures with this disposition. But, in other procedures, access by an anesthesiologist to the patient's head would be obstructed by the X-ray stand. Thus hospitals require roughly an equal number of installations with the table extending from the right and left sides of the beam so that the patient can be supported with his head to the beam for access by an anesthesiologist and equipment, and with the foot end of the table free for access by the X-ray stand, or vice versa.

Figure 3:
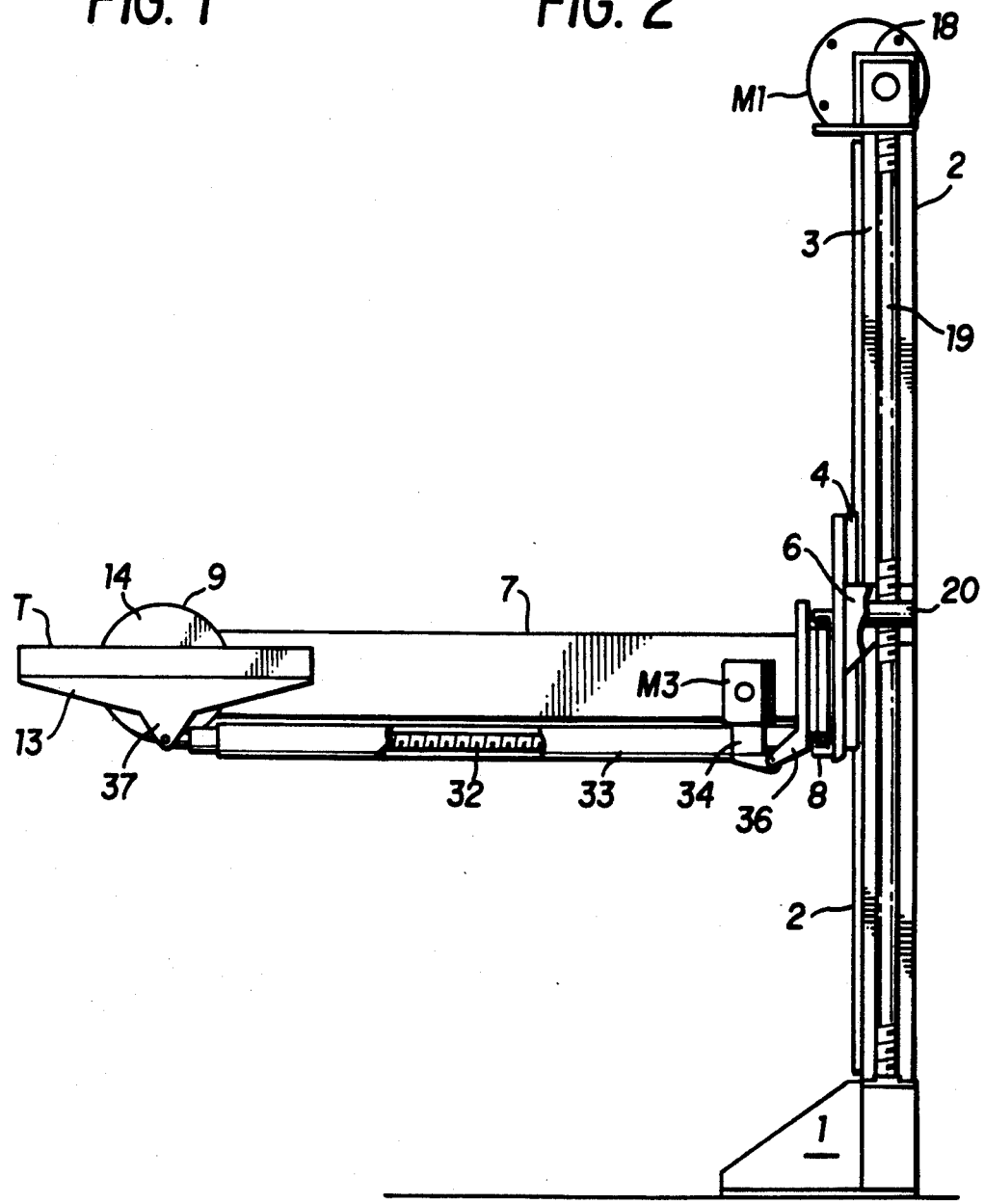
FIG. 3 is a right side elevation of the support apparatus.
Figure 7:
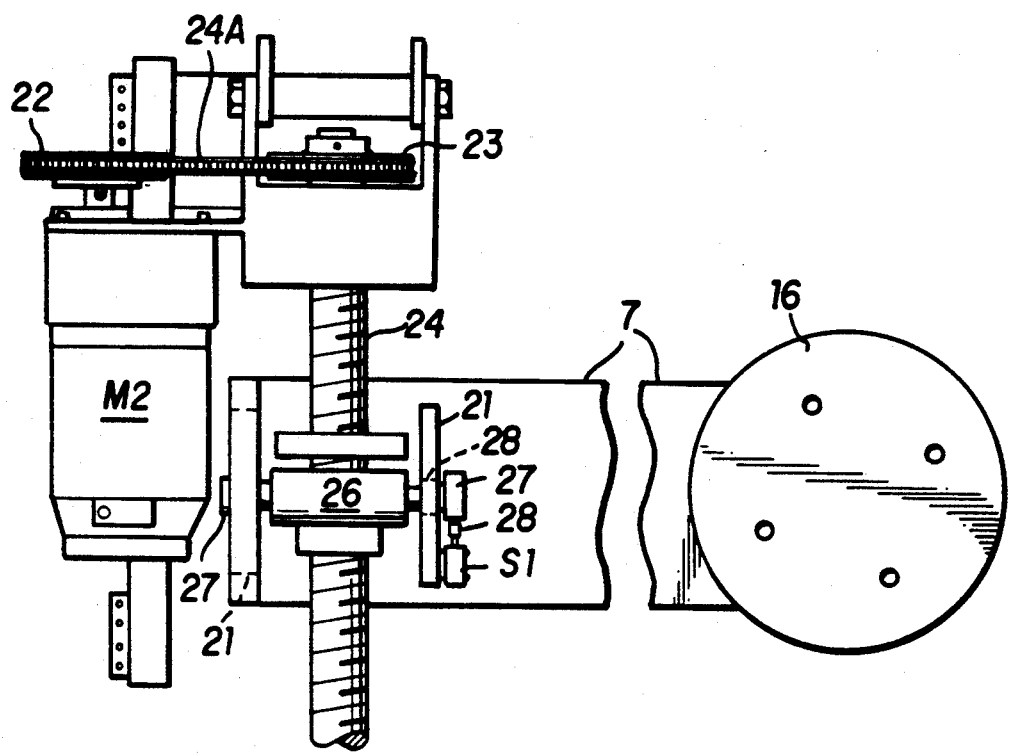
FIG. 7 is an enlarged left side elevation of a detail of FIG. 4.

The structure of apparatus for supporting a patient during the medical procedure is shown generally in FIGS. 3, 4 and 7 and comprises a base 1 anchored on an operating room floor, with an upright standard 2. The standard has vertical rails 3 which are engaged by linear bearings 4 on an elevator carriage 6 which rides up and down on the rails. On the carriage 6 is a heavy duty rotary bearing 8 on which is attached a cantilever beam 7 whose longitudinal axis extends horizontally from the standard. At its free end the cantilever beam 7 forms a cylindrical collar 9 extending at right angles to the beam with a continuous diameter and with identical open ends.

Figure 8:
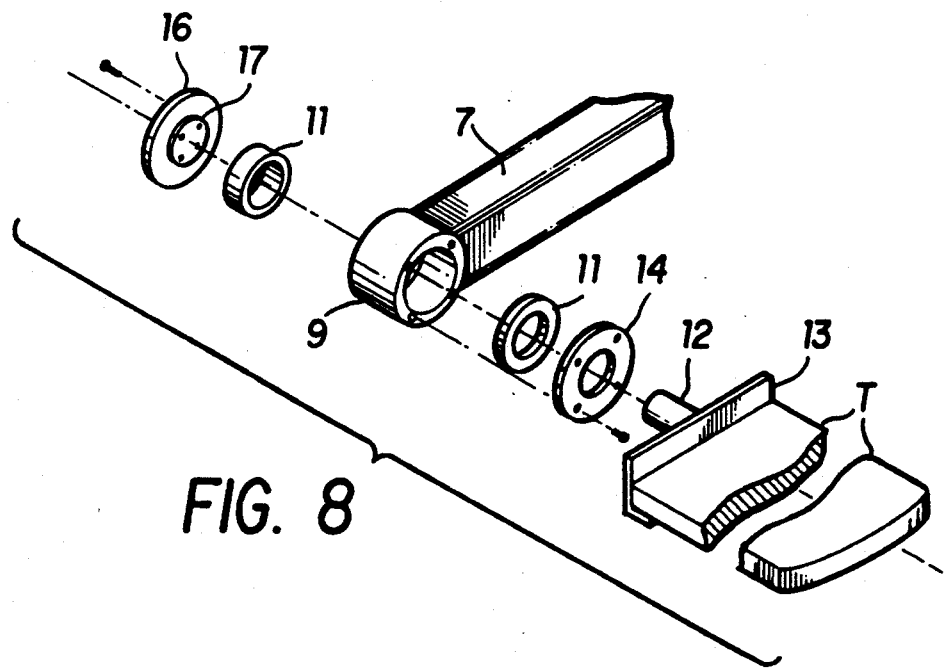
FIG. 8 is an exploded isometric view of the attachment of the patient support table to the cantilever beam.

As shown exploded in FIG. 8 the collar is adapted to receive two rotary bearings 11 in which is journalled the stub shaft 12 of a table bracket 13. One end of the collar is closed by an apertured disk 14 screwed to the collar, and the other end is closed by a circular plate 16 with a circular boss 17 screwed to the stub shaft 12. Secured to the bracket 13 is a table top T adapted to support the patient under examination and extending at a right angle to the longitudinal axis of the beam 7.

Mounted at the top of the standard 2 is a first motor M1 which, through a gear box 18, drives a screw 19 engaging a nut 20 on the carriage so as to raise and lower the carriage and the patient table.

As shown particularly in FIGS. 4, 5 and 7, a double crank arm 21 welded to the beam 7 extends laterally from the beam parallel to the carriage 6. A second, tilt motor M2 (FIGS. 4 and 7), through sprockets 22 and 23 and a connecting chain, drives a screw threaded through a nut 26 pivotally secured between the two arms of the crank 21 by a pin 27. When energized the second motor rotates the beam about its longitudinal axis so as to effect Trendelenburg tilting of the patient table about an axis transverse of the patient.

As shown in FIG. 3, a third, cant motor M3 is mounted on the side of the beam from which the table extends. Through a gear box 31 the third motor drives a screw 32 confined in a tubular housing 33. One end of the housing is pivotally anchored in a yoke 36 on the end of the beam, and the other end is pivotally connected to an extension 37 from the rotating bracket 13 on which the table T is mounted. Reversible drive of the third motor M3 rotates the bracket in the beam collar 9 and cants the table and patient about the axis of the collar which is substantially the same as the longitudinal axis of the patient.

Reverting to FIGS. 5 and 6, the pin 27 connecting the drive screw 24 of the second motor M2 to the beam crank arms 21 loosely engages in a slot 28 in the crank arms such that the weight of the patient table reflected back through the beam lifts the slot in the crank arms upwardly against the pin 27 at the lower end of the slot. In this position the enlarged end of the pin engages the contact 29 of a spring collision switch S1 attached to one of the crank arms adjacent the slot thereby holding the switch open (FIGS. 4, 5 and 6). If, during a critical procedure with a patient on the table, the table should be driven by any one of the three motors M1, M2 or M3 into collision with any obstruction below the table, the table would be lifted relative to the beam causing the beam crank arm 21 to rotate the collision switch S1 away from engagement with the pin 27 thus allowing the collision switch to close and energize a relay 33. The relay would then open its contacts 34, 35 and 36 between a motor control circuit 37 and the respective motors disabling all of them (with the exception that the motor control circuit would allow the first motor M1 to raise the patient table away from collision).

Thus, no matter which one or combination of the three motors necessary to provide elevation, tilting and canting causes the collision, the single collision switch on the beam crank arm will detect the collision and arrest it instantly.

It should be understood that the present disclosure is for the purpose of illustration only and that the present invention includes all modifications and equivalents falling within the appended claims.

I claim:

1. Apparatus for supporting a patient during medical procedures comprising:
   a base with an upright standard;
   a patient table having a longitudinal and a transverse axis;
   a table support on the standard, the support including a single beam extending from the support to one corner of the table, and the beam constituting a sole, cantilever support for the table;
   first rotational means on the support rotationally mounting one end of the beam so as to tilt the table about a first axis;
   and second rotational means on the support for rotating the table about a second axis at right angles to the first axis, and constituting a rotary bearing coupling the beam to the table so that the table can be tilted about its transverse axis and canted about its longitudinal axis;
   the beam extending from the standard to one end of the table a substantial distance sufficient to leave the supported end of the table unobstructed to medical personel.

2. Apparatus according to claim 1 wherein the second rotational means comprises bearing means at the end of the shaft rotatively mounting the table on the shaft.

3. Apparatus according to claim 2 including a bell crank connected to the table.

4. Apparatus according to claim 3 including a rod extending the length of the shaft from drive means on the base to the bell crank for turning the table about the second axis.

* * * * *